United States Patent
Endo et al.

(10) Patent No.: US 8,777,842 B2
(45) Date of Patent: Jul. 15, 2014

(54) ENDOSCOPE ASSEMBLY

(75) Inventors: Takahisa Endo, Tachikawa (JP); Ryohei Kagawa, Hachioji (JP)

(73) Assignees: Olympus Corporation, Tokyo (JP); Olympus Medical Systems Corp., Tokyo (JP)

( * ) Notice: Subject to any disclaimer, the term of this patent is extended or adjusted under 35 U.S.C. 154(b) by 1087 days.

(21) Appl. No.: 12/362,220

(22) Filed: Jan. 29, 2009

(65) Prior Publication Data

US 2009/0209810 A1 Aug. 20, 2009

(30) Foreign Application Priority Data

Feb. 15, 2008 (JP) ................................. 2008-035220

(51) Int. Cl.
*A61B 1/00* (2006.01)
*A61B 1/04* (2006.01)

(52) U.S. Cl.
USPC .......................................... 600/118; 600/117

(58) Field of Classification Search
USPC .................................................. 600/117, 118
See application file for complete search history.

(56) References Cited

U.S. PATENT DOCUMENTS

| | | | | |
|---|---|---|---|---|
| 4,633,304 A | * | 12/1986 | Nagasaki | 348/69 |
| 4,870,950 A | * | 10/1989 | Kanbara et al. | 600/109 |
| 6,636,254 B1 | * | 10/2003 | Onishi et al. | 348/65 |
| 2008/0100699 A1 | * | 5/2008 | Hibi | 348/65 |

FOREIGN PATENT DOCUMENTS

| | | | |
|---|---|---|---|
| JP | 2001-292961 A | | 10/2001 |
| JP | 2006333269 A | * | 12/2006 |
| JP | 2007-81741 A | | 3/2007 |

OTHER PUBLICATIONS

Japanese Office Action dated Sep. 4, 2012, issued in corresponding Japanese patent application No. 2008-035220, w/ English translation.

* cited by examiner

*Primary Examiner* — Anhtuan T Nguyen
*Assistant Examiner* — Rynae Boler
(74) *Attorney, Agent, or Firm* — Westerman, Hattori, Daniels & Adrian, LLP

(57) ABSTRACT

An endoscope assembly communicates with a data processing unit by radio waves. The endoscope assembly includes operation switches, which is configured to be operated by an operator, and a control unit. The control unit is configured to enable the operation switches to function as switches for setting wireless communication when connection for wireless communication with the data processing unit is not established. Further, the control unit is configured to enable the operation switches to function as switches for inherent operations including at least an image acquisition operation when connection for wireless communication with the data processing unit is established.

4 Claims, 5 Drawing Sheets

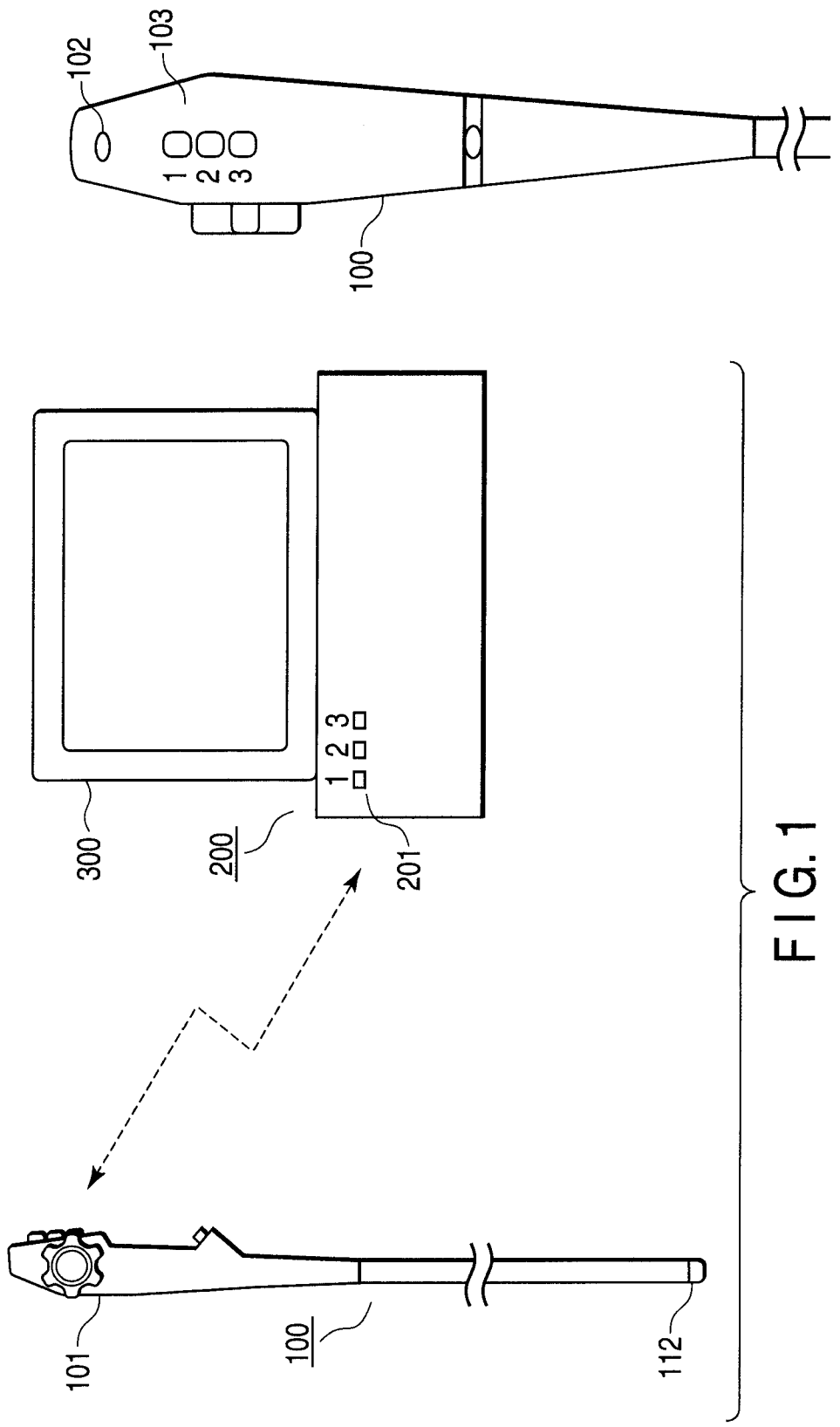

| Switch No. | Operation | Communication setting | | |
|---|---|---|---|---|
| | | Channel | SSID | WEP |
| 1 | Communication setting | 1 | ID_A | WEP1 |
| 2 | Communication setting | 7 | ID_B | WEP2 |
| 3 | Communication setting | 13 | ID_C | WEP3 |

| Switch No. | Operation |
|---|---|
| 1 | Freeze |
| 2 | Save frozen image |
| 3 | Reverse image |

ENDOSCOPE ASSEMBLY

CROSS-REFERENCE TO RELATED APPLICATIONS

This application is based upon and claims the benefit of priority from prior Japanese Patent Application No. 2008-035220, filed Feb. 15, 2008, the entire contents of which are incorporated herein by reference.

BACKGROUND OF THE INVENTION

1. Field of the Invention

The present invention relates to an endoscope assembly, which is inserted into a patient's body for performing inherent operations including at least an image acquisition operation.

2. Description of the Related Art

In recent years, there has been widely used an endoscope system which can observe an image of a subject in an abdominal cavity or path by inserting a slender insertion tube part into an abdominal cavity or path.

Such an endoscope system generally comprises an endoscope assembly, a light source unit, a light guide cable, an image acquisition unit, a video processor, a signal cable, and a monitor unit. The endoscope assembly has an insertion tube part, which is inserted into an abdominal cavity or path. The light source unit is provided separately from the endoscope assembly, and supplies an illumination light to the endoscope assembly. The light guide cable leads the illumination light from the light source unit to the endoscope assembly. The image acquisition unit is built in or removably provided in the endoscope assembly, and captures a subject and obtains its image data. The video processor is provided separately from the endoscope assembly, and converts the image data obtained by the endoscope assembly into a video signal displayable on a monitor. The signal cable is used to transmit the image data from the endoscope assembly to the video processor. The monitor unit displays the video signal obtained by the video processor. Therefore, the endoscope assembly is connected to the light source unit and video processor, which are external units, through the light guide cable and the signal cable. This limits a movable range of the endoscope assembly, and disturbs the operability of the endoscope assembly.

Under the circumstances, U.S. Pat. No. 4,633,304 discloses the following endoscope system. In this endoscope system, an illumination unit comprising a light-emitting diode (LED) is incorporated in an endoscope assembly. Thereby, a light guide cable extended from an endoscope assembly is eliminated. The endoscope assembly is provided with a video signal processing circuit, which obtains a video signal displayable on a monitor by processing image data, and a transmission circuit, which transmits the video signal by radio waves. A data processing unit, which receives the radio waves from the transmission circuit, and demodulates the video signal, is provided separately from the endoscope assembly. Thereby, a signal cable extended from the endoscope assembly is eliminated. Such an endoscope system is generally called a wireless endoscope system, and has advantages that a movable range of the endoscope assembly is not limited, and the operability of the endoscope assembly is improved.

BRIEF SUMMARY OF THE INVENTION

According to an aspect of the present invention, there is provided an endoscope assembly which communicates with a data processing unit by radio waves, comprising:

operation switches configured to be operated by an operator; and a control unit configured to enable the operation switches to function as switches for setting wireless communication when connection for wireless communication with the data processing unit is not established, and to function as switches for inherent operations including at least an image acquisition operation when connection for wireless communication with the data processing unit is established.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a diagram showing a configuration of a wireless endoscope system adopting an endoscope assembly according to an embodiment of the present invention;

FIG. 2 is an external view of the endoscope assembly viewed from the side, on which operation switches are provided;

DETAILED DESCRIPTION OF THE INVENTION

Figures 3, 4, 5:
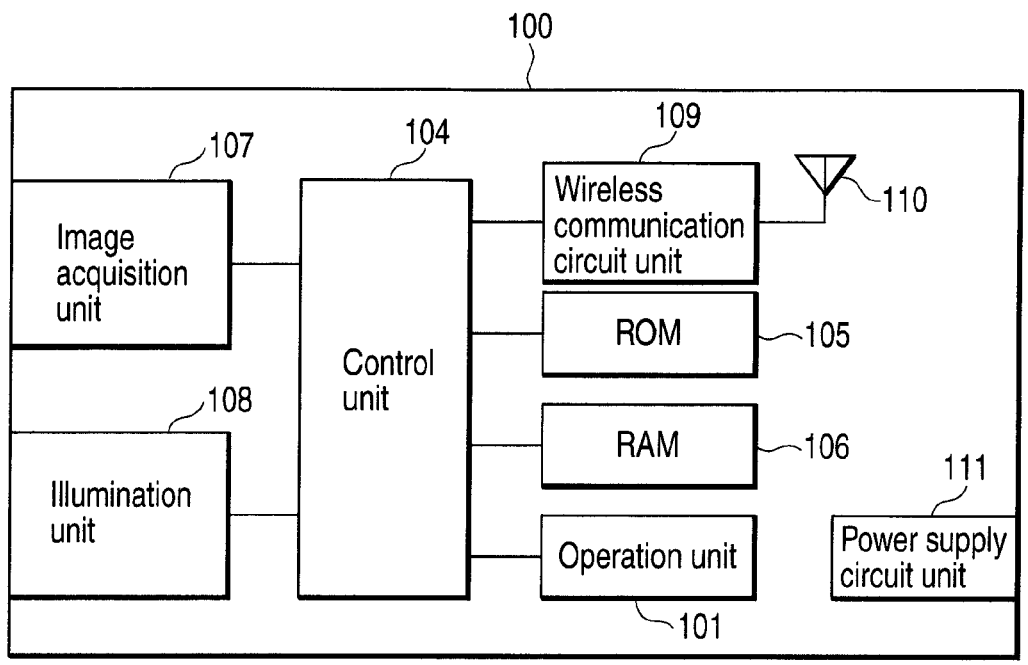
FIG. 3 is a block diagram showing an electrical configuration of the endoscope assembly.
FIG. 4 is a table showing parameters for communication setting.
FIG. 5 is a table showing parameters for inherent operations including at least an image acquisition operation.

Hereinafter, a best embodiment of the present invention will be explained with reference to the accompanying drawings.

As shown in FIG. 1, a wireless endoscope system adopting an endoscope assembly according to an embodiment of the invention comprises an endoscope assembly 100 according to an embodiment of the invention, and a data processing unit 200. The endoscope assembly 100 transmits captured image data by wireless communication as indicated by a broken line in the drawing. The data processing unit 200 receives the image data from the endoscope assembly 100, and displays the data on a monitor unit 300. The data processing unit 200 is provided with communication setting indicators 201 comprising LEDS to indicate states of communication setting of the data processing unit 200.

The endoscope assembly 100 is provided with an operation unit 101 comprising switches for inputting operational instructions into the endoscope system. The operation unit 101 has a power switch 102 and operation switches 103, as shown in FIG. 2. The operation switches 103 are given numbers to discriminate the switches.

Electrically, the endoscope assembly 100 is provided with a control unit 104, as shown in FIG. 3, which is connected to a ROM 105, a RAM 106, an image acquisition unit 107, an illumination unit 108, a wireless communication circuit unit 109, and the above-mentioned operation unit 101. An antenna 110 is connected to the wireless communication circuit unit 109. The endoscope assembly 100 has a power supply circuit unit 111, which supplies power to each of the above-mentioned components.

The control unit 104 is a unit to perform sequence control of the endoscope assembly 100, and is operated according to a program stored in the ROM 105.

The ROM 105 is a nonvolatile memory such as a flash ROM, and stores program data for control of the endoscope assembly 100 and various setting information including parameters for communication setting. The ROM 105 is also used as an area for storing the data of a parameter table 105A for communication setting and a parameter table 105B for inherent operations, the inherent operations including at least an image acquisition operation (a frozen image saving operation).

In the parameter table 105A for communication setting, operations and communication setting (channel, SSID, WEP) are stored for each switch number as shown in FIG. 4. In the parameter table 105B for inherent operations, operations are stored for each switch number as shown in FIG. 5.

The RAM 106 is used as an area for temporarily buffering the image data output from the image acquisition unit 107, a work area used for arithmetic operations in the control unit 104, and an area for temporarily storing various setting. The RAM 106 is also used as an area for storing the data of a parameter table for operations of the operation switches, and as an area for storing parameters for communication setting.

Though not especially shown in the drawing, the image acquisition unit 107 comprises a lens, a photoelectric converter, an analog-to-digital converter, and a video processor. The lens forms an image of incident light on the photoelectric converter. The photoelectric converter is a CCD or a CMOS sensor, which converts the formed image of the incident light into an electric signal. The analog-to-digital converter converts an analog electric signal output from the photoelectric converter, into a digital electric signal. The video processor generates image data by processing the digital electric signal from the analog-to-digital converter.

Though not especially shown in the drawing, the illumination unit 108 comprises an illumination lens disposed in a distal end portion 112 (refer to FIG. 1) of the endoscope assembly 100, an LED disposed in the distal end portion 112, and a LED driving circuit to drive the LED. The light emitted from the LED is applied to an observing part in the abdominal cavity of a patient through the illumination lens. The LED may be disposed in the operation unit 101, not in the distal end portion 112, and the light from the LED may be guided to the distal end portion 112 through the light guide.

Though not especially shown in the drawing, the wireless communication circuit unit 109 comprises a high frequency circuit necessary for wireless communication, an encoding/decoding circuit, and a buffer memory for wireless communication. In this embodiment, a wireless LAN protocol IEEE802.11 is used as a wireless communication system. For wireless communication with the data processing unit 200, it is necessary to set the same channel (frequency in use), SSID and WEP as the communication setting set in the data processing unit 200.

As described above, the operation unit 101 comprises the power switch 102 and operation switches 103, and outputs a state and a change in the state of these button and switches as an electric signal. The operation switches 103 operate as selector switches to select communication setting, until a connection for communication is established. After a connection for communication is established, the operation switches operate as switches to instruct operations during surgery, such as freezing an image, saving a still image, and reversing an image.

The power supply circuit unit 111, not especially shown in the drawing, comprises a battery and a DC/DC converter, and detects turning-on of the power switch 102, and supplies power to each of the above-described components.

Figure 6:
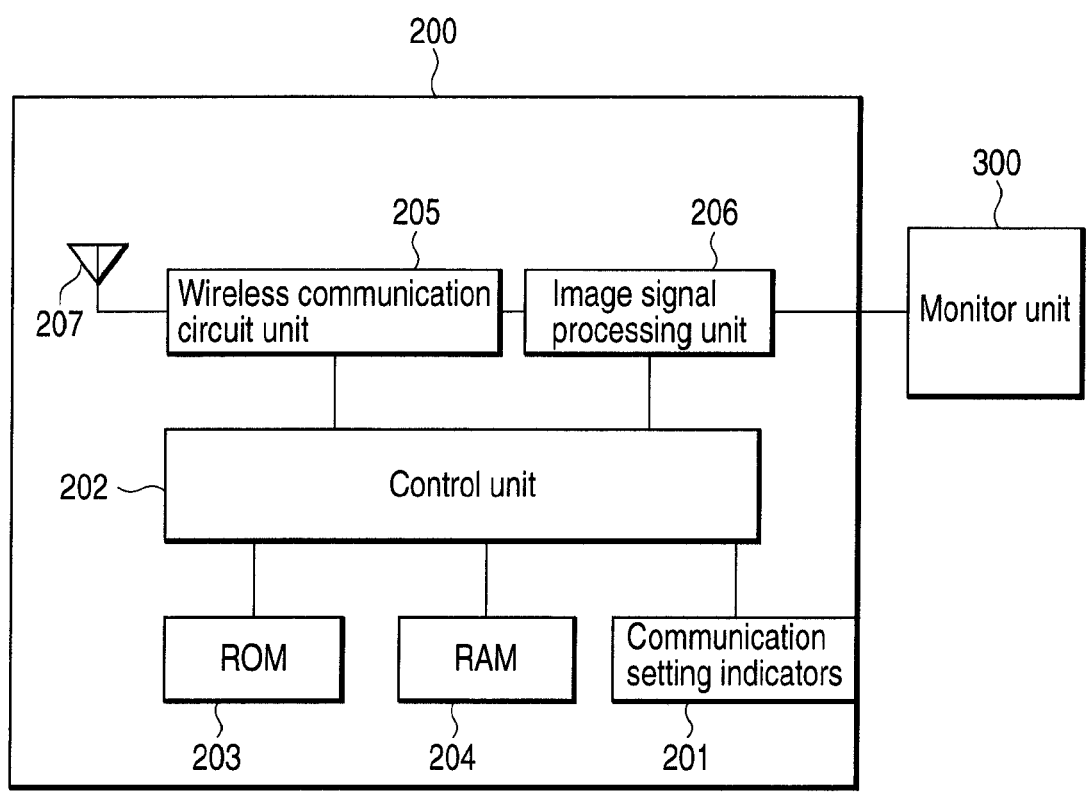
FIG. 6 is a block diagram of a data processing unit.

In contrast, the data processing unit 200 includes a control unit 202, which is connected to a ROM 203, a RAM 204, a wireless communication circuit unit 205, an image signal processing unit 206, and the above-described communication setting indicators 201, as shown in FIG. 6. An antenna 207 is connected to the wireless communication circuit unit 205. The wireless communication circuit unit 205 is connected to the above-described image signal processing unit 206. The image signal processing unit 206 is connected to the above-described monitor unit 300.

The control unit 202 is a unit to perform sequence control of the data processing unit 200, and is operated according to a program stored in the ROM 203.

The ROM 203 is a nonvolatile memory such as a flash ROM, and stores program data and various setting information for controlling the data processing unit 200.

The RAM 204 is used as an area for temporarily buffering image data received by the wireless communication circuit unit 205, a work area used for arithmetic operations in the control unit 202, and an area for temporarily storing various setting.

The wireless communication circuit unit 205, not especially shown in the drawing, comprises a high frequency circuit unit necessary for wireless communication, an encoding/decoding circuit unit, and a buffer memory for wireless communication. Like the wireless communication circuit unit 109 in the endoscope assembly 100, the wireless communication circuit unit 205 performs wireless communication according to a wireless LAN protocol.

The image signal processing unit 206 converts the image data received by the wireless communication circuit unit 205, into a video signal such as an NTSC signal or a PAL signal, and outputs the signal to the monitor unit 300.

The communication setting indicators 201 comprise a plurality of LED to indicate communication setting states of the data processing unit 200, as described before. The surface of the data processing unit 200 is marked with numbers, for example, close to the LEDS to discriminate each LED.

The monitor unit 300 comprises a liquid crystal display unit, for example, and its control circuit.

Figure 7:
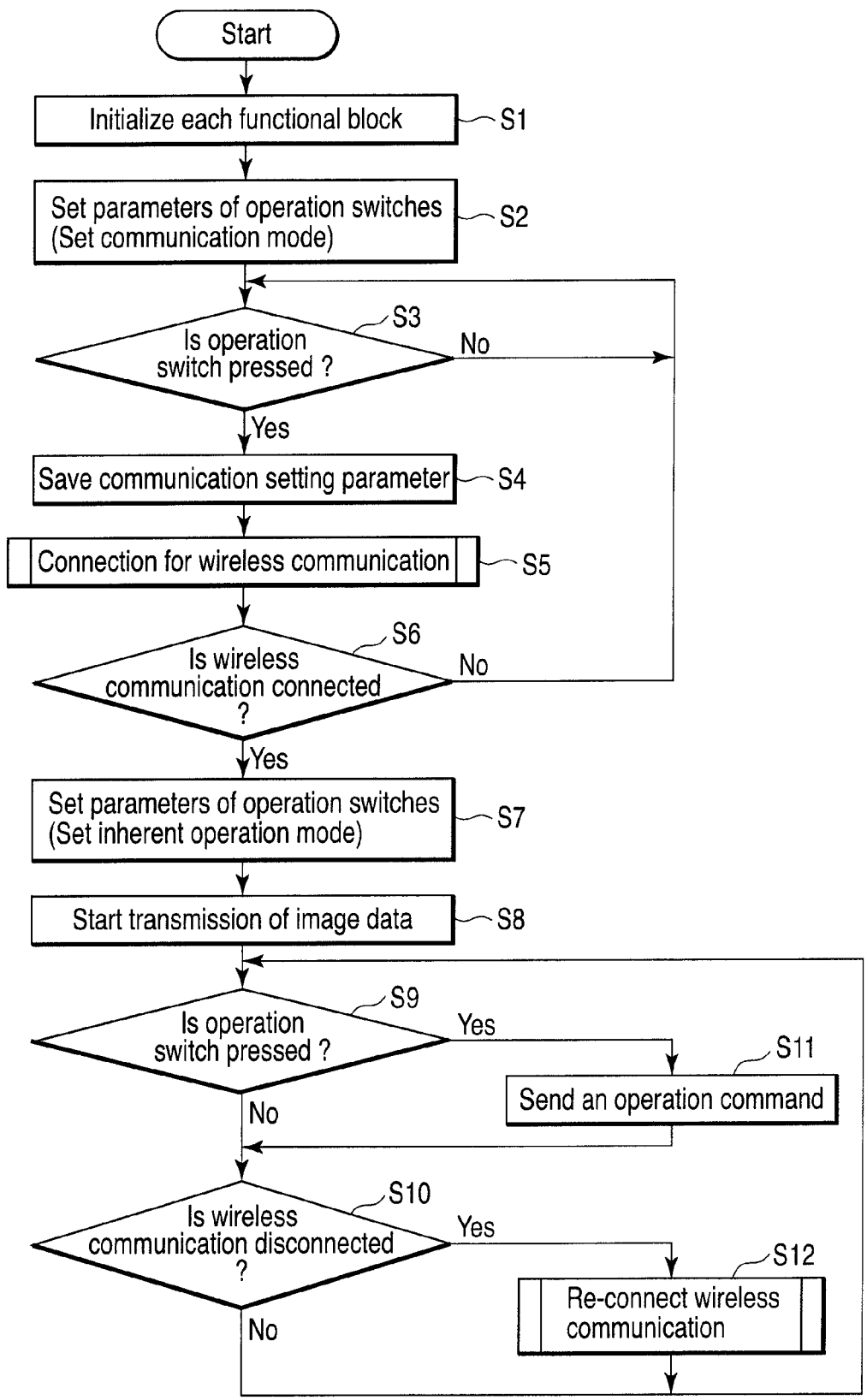
FIG. 7 is a flowchart showing operations of the endoscope assembly.

Next, an explanation will be give of the operation of the wireless endoscope system including the endoscope assembly according to this embodiment, with reference to FIG. 7.

It is assumed that an appropriate communication setting has been made in the data processing unit 200 upon installation, according to wireless communication conditions at the installation site. When the power of the data processing unit 200 is turned on, the communication setting made in the data processing unit 200 is indicated by the communication setting indicator 201, and the unit is set to a state waiting for making connection for communication from the endoscope assembly 100. For example, in a state in which a first setting out of three kinds of communication setting is set, the LED indicated by a number "1" out of three LEDS of the communication setting indicator 201 is lit.

In the above situation, when the power switch 102 of the endoscope assembly 100 is turned on, the control unit 104 of the endoscope assembly 100 initializes each function block of the endoscope assembly 100 (step S1). Thereafter, the control unit 104 sets the parameter table 105A for communication setting stored in the ROM 105, shown in FIG. 4, on the parameter table for operations of the operation switches provided in the RAM 106 (step S2). Then, the control unit waits for operations of the operation switches 103 in the operation unit 101 (step S3).

An operator confirms the state of communication setting indicated by the communication setting indicator 201 of the data processing unit 200, and operates the operation switch 103 according to the indicated state. For example, when the LED "1" of the communication setting indicators 201 is lit, the operator operates the operation switch 103 numbered "1."

When the operation switch 103 is operated, the control unit 104 saves parameters for communication setting in the RAM 106 (step S4). This is performed as follows. The control unit 104 reads the communication setting (channel, SSID, WEP) corresponding to the operated operation switch 103, from the parameter table 105A for communication setting that is set on the parameter table for operations of the operation switches provided in the RAM 106. The read communication setting is saved in the RAM 106 as a communication setting parameter.

Figure 8:
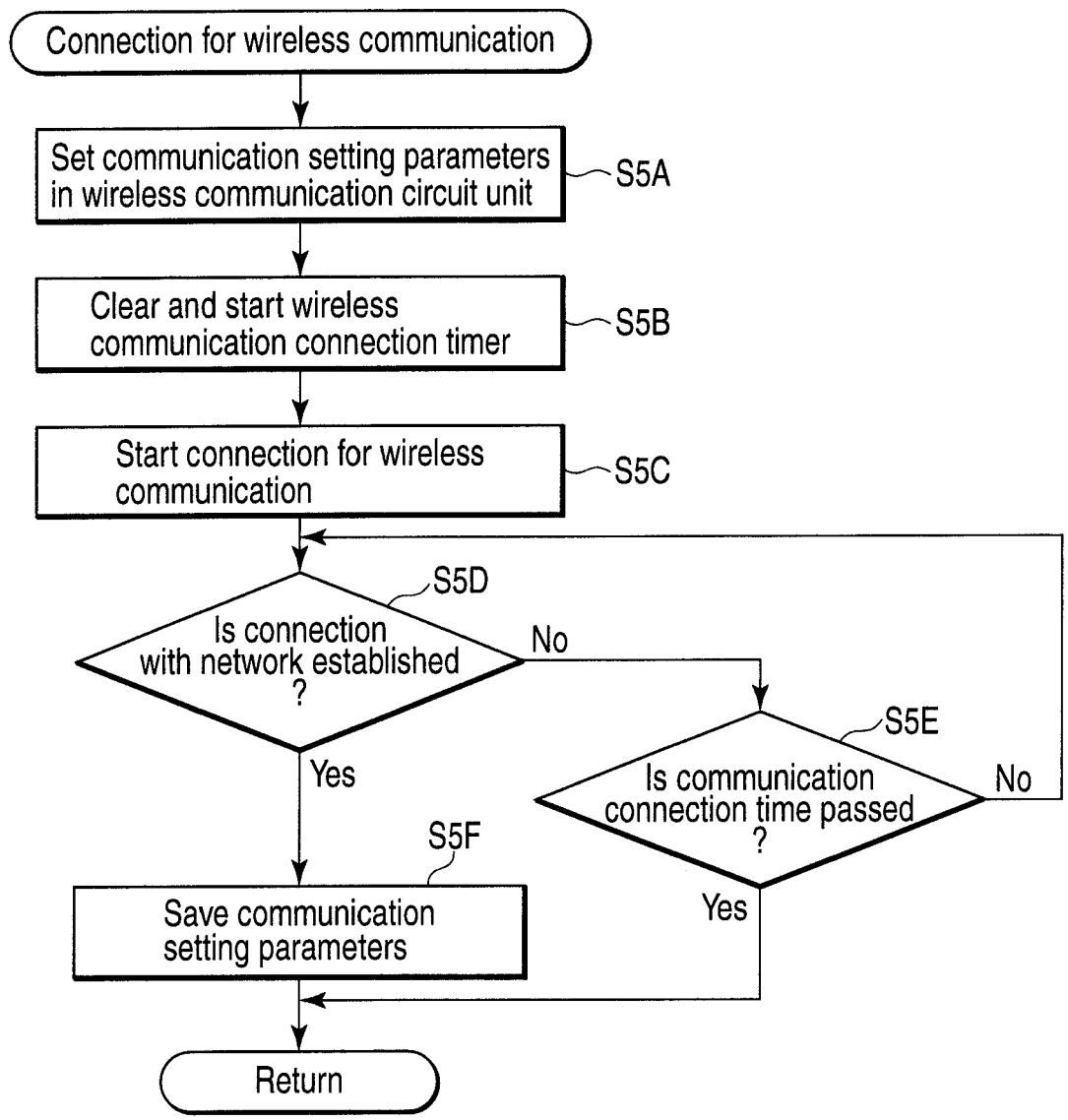
FIG. 8 is a detailed flowchart showing connection for wireless communication.

After the communication setting parameter is saved in this manner, the control unit 104 makes connection for wireless communication with the data processing unit 200 (step S5). This connection for wireless communication is made as shown in FIG. 8.

At first, the communication setting parameter saved in the RAM 106 is set in the wireless communication circuit unit 109 (step S5A). Then, a not-shown wireless communication connection timer provided in the control unit 104 is cleared, and started (step S5B). Connection for wireless communication with the data processing unit 200 is started by the wireless communication circuit unit 109 (step S5C).

Thereafter, whether or not the wireless communication with the data processing unit 200 is established, or whether the connection to a network is established, is determined, as the wireless communication is performed according to the wireless LAN protocol in this embodiment (step S5D).

If non-establishment of the connection to a network is determined at this time, whether the wireless communication connection timer indicates a predetermined time, or whether the communication connection time has passed, is determined (step S5E). If the communication connection time has not pass, the operation returns to step S5D.

When the wireless communication with the data processing unit 200 is established, and establishment of the connection to a network is determined in step S5D, the current communication setting parameter is saved in a predetermined area of the RAM 106 (step S5F). Then, the operation returns to a higher-order routine.

In contrast, if passage of the communication connection time without establishing the connection to a network is determined in step S5E, the operation returns to a higher-order routine without saving the communication setting parameter in step S5F.

The control unit 104 determines whether or not the connection for wireless communication between the endoscope and data processing unit 200 is established (step S6).

If non-establishment of the connection for wireless communication is determined, the operation returns to step S3, and operation of the operation switch is waited. Therefore, in this case, the operator tries again to establish the connection for wireless communication, by operating the operation switch 103 according to the state of communication setting indicated by the communication setting indicator 201 of the data processing unit 200, or by operating another operation switch 103.

In contrast, if establishment of the connection for wireless communication is determined in step S6, the control unit 104 sets the parameter table 105B for inherent operations stored in the ROM 105, shown in FIG. 5, on the parameter table for operations of the operation switches provided in the RAM 106 (step S7). Then, the control unit starts transmission of the image data captured by the image acquisition unit 107 (step s8).

Then, the control unit 104 waits for operations of the operation switches 103 in the operation unit 101 (step S9). However, in this case, a step of checking whether the wireless communication is disconnected is inserted in the period waiting for the operation (step S10).

In this state, the image data is sent from the endoscope assembly 100 to the data processing unit 200 by wireless communication, and the operator inserts the distal end portion 112 of the endoscope assembly 100 into the abdominal cavity of a patient, while confirming the image data displayed on the monitor unit 300.

When the distal end portion 112 of the endoscope assembly 100 reaches a desired position/attitude, the operator operates the operation switch 103 of the operation unit 101.

When the operation switch 103 is operated, the control unit 104 transmits an operation command (step S11). Namely, the control unit 104 reads a parameter for an inherent operation (operation content) corresponding to the operated operation switch 103, from the parameter table 105B for inherent operations including at least an image acquisition operation, which is set in the parameter table for operations of the operation switches provided in the RAM 106. The control unit 104 sends the read parameter for an inherent operation from the wireless communication circuit unit 109 to the data processing unit 200, as an operation command.

As described above, a loop of step S9 (and step S11) and step S10 is repeated, and an operation command corresponding to the operated operation switch 103 of the operation unit 101 is sent to the data processing unit 200, until the power switch 102 of the operation unit 101 is turned off.

If disconnection of wireless communication due to deterioration of radio wave condition is determined in step S10, the control unit 104 shifts to a process of re-connecting wireless communication (step S12).

Details of the re-connection process are the same as the connection for wireless communication described above with reference to FIG. 8. However, in the re-connection process, communication is establish by using a communication setting parameter saved in a predetermined area of the RAM 106, in the above-described step S5F of making connection for wireless communication, and the selection of communication setting by the operation switch 103 of the operation unit 101 is not performed. Further, in the re-connection process, the operation of step S5F of saving a current communication setting parameter in a predetermined area in the RAM 106 may be eliminated.

As described herein, according to the embodiment, the operation switches 103 of the operation unit 101 function as switches for setting communication, before communication is established, and function as operation switches for inherent operations including at least an image acquisition operation after communication is established. Therefore, it is unnecessary to provide a switch dedicated to communication setting, thereby saving the space and reducing the cost.

As the operation switches 103 function as switches for inherent operations including at least an image acquisition operation after wireless communication is connected, a change in communication setting due to an operating error during inherent operations of the endoscope assembly 100 can be prevented.

Further, when connection for wireless communication is established, the communication setting parameter at that time is stored in the RAM 106, and the communication is re-connected by using the stored communication setting parameter. Therefore, if wireless communication is disconnected due to deterioration of radio wave condition, the communication can be easily re-connected without operating the operation switch 103.

Furthermore, when the connection for wireless communication has been established, the operation switch 103 functions as an operation switch for the image data captured by the image acquisition unit 107, and the image data can be processed by operating the operation switch 103.

Hereinbefore, the present invention has been explained based on one embodiment. The invention is not limited to the above-described embodiment. Various modification and applications are of course possible within essential characteristics of the invention.

For example, the image acquisition unit 107 includes a video processor, and image data is sent to the data processing unit 200 by radio waves, in the description herein. A video processor may be provided in the data processing unit 200, and a digital electric signal may be sent by radio waves.

Further, the communication setting indicators 201 may not be provided in the data processing unit 200, and communication setting may be displayed as an image on the monitor unit 300 according to a command from the endoscope assembly 100.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope assembly which communicates with a data processing unit by radio waves, comprising:
   a power switch;
   an image acquisition unit configured to acquire and output an image data;
   operation switches configured to be operated by an operator;
   a control unit configured to set a function of the operation switches to a function for operating the wireless communication setting until the connection for wireless communication with the data processing unit is established after switching on the power switch, and to switch the function of the operation switches from the function for operating the wireless communication setting to a function for operating the image data after the connection for wireless communication with the data processing unit is established; and
   a storage unit configured to store parameters for operating the wireless communication setting and parameters for operating the image data, wherein
   the control unit is further configured to set the parameters for operating the wireless communication setting stored in the storage unit as operation parameters for the operation switches during a period from a time when the power switch has been turned on to a time when the connection for wireless communication with the data processing unit is established, and to set the parameters for operating the image data as the operation parameters for the operation switches after the connection for wireless communication with the data processing unit has been established,
   switch numerals are assigned to the operation switches,
   the storage unit is further configured to store a parameter table for communication in which the switch numerals are associated with the parameters for operating the wireless communication setting and a parameter table for image operation in which the switch numerals are associated with the parameters for operating the image data, and
   the control unit is further configured to set the parameters for operating the wireless communication setting associated with the switch numerals of the operation switches in the parameter table for communication stored in the storage unit as the operation parameters for the operation switches during a period from a time when the power switch is turned on to a time when the connection for wireless communication with the data processing unit is established, and to set the parameters for operating the image data associated with the switch numerals of the operation switches in the parameter table for image operation stored in the storage unit as the operation parameters for the operation switches after the connection for wireless communication with the data processing unit has been established.

2. The endoscope assembly according to claim 1, wherein the storage unit is configured to store the setting for wireless communication, in which connection with the data processing unit is established, and
   when the established wireless communication is disconnected in a state in which the endoscope assembly is started, the control unit re-establishes the disconnected wireless connection by setting the wireless communication stored in the storage unit, while continuously enabling the operation switches to function as the switches for operations of the image data.

3. The endoscope assembly according to claim 1, wherein the control unit enables the switches for operations of the image data to function as the image acquisition operation, an image freeze operation, and an image reverse operation.

4. The endoscope assembly according to claim 1, further comprising:
   a wireless transmitting unit configured to start wireless transmission of the image data to the data processing unit after the connection for wireless communication with the data processing unit is established, and to transmit operation commands corresponding to the operation switches when the operation switches are operated.

* * * * *